US012089918B2

(12) United States Patent
Sharma et al.

(10) Patent No.: US 12,089,918 B2
(45) Date of Patent: Sep. 17, 2024

(54) SYSTEM AND METHOD FOR MACHINE LEARNING BASED MAPPING FUNCTION OF PATIENT DATA FROM ONE PHYSIOLOGICAL STATE TO ANOTHER BASED ON COMPUTATIONAL FLUID DYNAMICS SIMULATION OF BLOOD VIA OFFLINE TRAINING

(71) Applicant: SIEMENS HEALTHINEERS AG, Forchheim (DE)

(72) Inventors: Puneet Sharma, Princeton Junction, NJ (US); Lucian Mihai Itu, Brasov (RO); Saikiran Rapaka, Pennington, NJ (US); Frank Sauer, Princeton, NJ (US)

(73) Assignee: Siemens Healthineers AG, Forchheim (DE)

( * ) Notice: Subject to any disclaimer, the term of this patent is extended or adjusted under 35 U.S.C. 154(b) by 450 days.

(21) Appl. No.: 17/070,993

(22) Filed: Oct. 15, 2020

(65) Prior Publication Data

US 2021/0027466 A1   Jan. 28, 2021

Related U.S. Application Data

(62) Division of application No. 14/599,678, filed on Jan. 19, 2015, now abandoned.
(Continued)

(51) Int. Cl.
*A61B 5/02* (2006.01)
*A61B 5/00* (2006.01)
(Continued)

(52) U.S. Cl.
CPC ...... *A61B 5/02007* (2013.01); *A61B 5/02028* (2013.01); *A61B 5/021* (2013.01);
(Continued)

(58) Field of Classification Search
CPC . A61B 5/02007; A61B 5/02028; A61B 5/021; A61B 5/029; A61B 5/1128;
(Continued)

(56) References Cited

U.S. PATENT DOCUMENTS 7,302,096 B2   11/2007   Kim
8,386,188 B2   2/2013   Taylor et al.
(Continued)

FOREIGN PATENT DOCUMENTS

CN   1497494 A   5/2004
CN   102525443 A   7/2012
(Continued)

OTHER PUBLICATIONS

Office Action issued May 22, 2018 in corresponding Chinese Patent Application No. 201510288648.8.

*Primary Examiner* — Serkan Akar

(57) ABSTRACT

Systems and methods for determining a quantity of interest of a patient comprise receiving patient data of the patient at a first physiological state. A value of a quantity of interest of the patient at the first physiological state is determined based on the patient data. The quantity of interest represents a medical characteristic of the patient. Features are extracted from the patient data, wherein the features which are extracted are based on the quantity of interest to be determined for the patient at a second physiological state. The value of the quantity of interest of the patient at the first physiological state is mapped to a value of the quantity of interest of the patient at the second physiological state based on the extracted features.

12 Claims, 4 Drawing Sheets

Related U.S. Application Data

(60) Provisional application No. 62/004,294, filed on May 29, 2014.

(51) Int. Cl.
| | | |
|---|---|---|
| *A61B 5/021* | (2006.01) | |
| *A61B 5/029* | (2006.01) | |
| *A61B 5/11* | (2006.01) | |
| *A61B 6/03* | (2006.01) | |
| *G06F 18/214* | (2023.01) | |
| *G06F 18/2413* | (2023.01) | |
| *G06T 7/00* | (2017.01) | |
| *G16H 50/20* | (2018.01) | |

(52) U.S. Cl.
CPC ............ *A61B 5/029* (2013.01); *A61B 5/1128* (2013.01); *A61B 5/7275* (2013.01); *G06F 18/214* (2023.01); *G06F 18/2413* (2023.01); *G06T 7/0012* (2013.01); *G16H 50/20* (2018.01); *A61B 6/032* (2013.01); *A61B 2576/023* (2013.01)

(58) Field of Classification Search
CPC . A61B 5/7275; A61B 6/032; A61B 2576/023; G06F 18/214; G06F 18/2413; G06T 7/0012; G16H 50/20
See application file for complete search history.

(56) References Cited

U.S. PATENT DOCUMENTS

| | | |
|---|---|---|
| 8,655,817 B2 | 2/2014 | Hasey et al. |
| 9,119,540 B2 | 9/2015 | Sharma et al. |
| 9,999,361 B2 | 6/2018 | Sharma et al. |
| 2010/0191692 A1 | 7/2010 | Gassewitz et al. |
| 2012/0072190 A1 | 3/2012 | Sharma et al. |
| 2012/0176412 A1 | 7/2012 | Stuebe et al. |
| 2013/0116999 A1 | 5/2013 | Stein et al. |
| 2013/0246034 A1 | 9/2013 | Sharma et al. |
| 2014/0024932 A1 | 1/2014 | Sharma et al. |
| 2014/0058715 A1 | 2/2014 | Sharma et al. |
| 2014/0107935 A1 | 4/2014 | Taylor |
| 2015/0112901 A1* | 4/2015 | Singer ................. G06N 5/04 706/12 |
| 2015/0332111 A1* | 11/2015 | Kisilev ................. G16H 70/20 382/131 |

FOREIGN PATENT DOCUMENTS

| | | |
|---|---|---|
| CN | 103300820 A | 9/2013 |
| CN | 102525443 B | 5/2016 |
| WO | 9526006 A1 | 9/1995 |
| WO | 2005089641 A1 | 9/2005 |
| WO | 2013138428 A1 | 9/2013 |
| WO | 2013164462 A1 | 11/2013 |

* cited by examiner

SYSTEM AND METHOD FOR MACHINE LEARNING BASED MAPPING FUNCTION OF PATIENT DATA FROM ONE PHYSIOLOGICAL STATE TO ANOTHER BASED ON COMPUTATIONAL FLUID DYNAMICS SIMULATION OF BLOOD VIA OFFLINE TRAINING

This application is a divisional of U.S. patent application Ser. No. 14/599,678, filed Jan. 19, 2015, which claims the benefit of U.S. Provisional Application No. 62/004,294, filed May 29, 2014, the disclosures of which are herein incorporated by reference in their entirety.

BACKGROUND OF THE INVENTION

The present invention relates generally to representing a patient at a particular physiological state and more particularly to mapping patient data from one physiological state to another physiological state.

For clinical diagnosis, therapy planning, and prognosis, it is of interest to not only measure or compute data for a patient during a particular physiological state, but also to compare data for a patient at two or more different physiological states. For example, it is of interest to compare the role of a stenosis (in terms of pressure drop) when a patient is under different physiological conditions. Currently, the comparison of patient data at different physiological states can be achieved by either directly measuring the data of interest at each physiological state or by simulating each physiological state using appropriate boundary conditions for the model. However, these current solutions have drawbacks. The repeated measurement of the same data at different physiological states is not only costly, but requires an additional clinical procedure which may expose the patient to higher risk. In addition, in some instances, the measurement of data at different physiological states may not be practical since the primary purpose of the comparison would be to plan a therapy a priori and not just to assess it after it is administered. Similarly, the simulation of patient data for each physiological state using biophysical models may be time-consuming, resource-intensive, and prone to inaccuracies due to the difficulty in obtaining correct boundary conditions that represent a particular physiological state.

BRIEF SUMMARY OF THE INVENTION

In accordance with an embodiment, systems and methods for determining a quantity of interest of a patient comprise receiving patient data of the patient at a first physiological state. A value of a quantity of interest of the patient at the first physiological state is determined based on the patient data. The quantity of interest represents a medical characteristic of the patient. Features are extracted from the patient data, wherein the features which are extracted are based on the quantity of interest to be determined for the patient at a second physiological state. The value of the quantity of interest of the patient at the first physiological state is mapped to a value of the quantity of interest of the patient at the second physiological state based on the extracted features.

In one embodiment, the quantity of interest of the patient at the first physiological state is mapped to the quantity of interest of the patient at the second physiological state without using data of the patient at the second physiological state. The quantity of interest of the patient at the first physiological state may be a same quantity of interest as the quantity of interest of the patient at the second physiological state. The quantity of interest of the patient at the first physiological state may alternatively be different from the quantity of interest of the patient at the second physiological state.

The quantity of interest of the patient at the first physiological state may be mapped to the quantity of interest of the patient at the second physiological state by applying a trained mapping function to the value of the quantity of interest of the patient at the first state. The trained mapping function may represent a relationship between the quantity of interest of a set of patients at the first physiological state and the quantity of interest of the set of patients at the second physiological state. The trained mapping function may be determined in an offline step. The trained mapping function may be a machine-learning based mapping function trained based on training data comprising quantities of interest of the set of patient at the first physiological state and corresponding quantities of interest of the set of patients at the second physiological state. The training data may comprise simulated quantities of interest of the set of patients at the first physiological state and simulated corresponding quantities of interest at the second physiological state.

In some embodiments, systems and methods are provided for determining fractional flow reserve (FFR) for a coronary stenosis of a patient at a hyperemia state. Patient data of the patient at a rest state is received. A value of a pressure drop over the coronary stenosis of the patient at the rest state is calculated based on the patient data. Features are extracted from the patient data. The value of the pressure drop over the coronary stenosis of the patient at the rest state is mapped to a value of the pressure drop over the coronary stenosis of the patient at the hyperemia state based on the extracted features. The FFR for the coronary stenosis of the patient is outputted based on the pressure drop over the coronary stenosis of the patient at the hyperemia state.

These and other advantages of the invention will be apparent to those of ordinary skill in the art by reference to the following detailed description and the accompanying drawings.

DETAILED DESCRIPTION

The present invention relates to mapping patient data from one physiological state to another physiological state. Embodiments of the present invention are described herein to give a visual understanding of the method for mapping the patient data. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Figure 1:
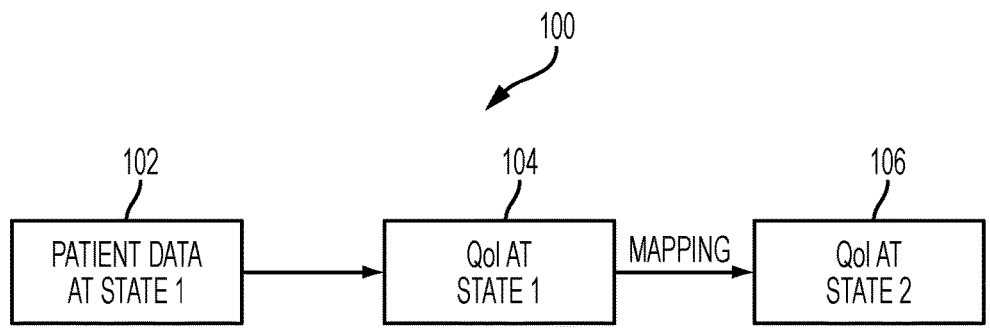
FIG. 1 shows a high-level framework for mapping patient data at one physiological state to another physiological state, in accordance with one embodiment.

FIG. 1 shows a high-level framework 100 for mapping patient data at one physiological state to another physiological state, in accordance with one or more embodiments. Framework 100 determines physiological data representing a patient at a particular state (i.e., State 2) based on data collected at a different state (i.e., State 1). The term "state," as used herein throughout the application, refers to a physiological condition of a patient. For example, State 1 may represent a baseline condition when the patient is at rest, while State 2 may represent a condition when the patient is under exertion due to, e.g., physical activity, an administered drug, etc. Framework 100 may be performed within a computer system using data stored within the computer system to provide a user with fast access to information that can, e.g., impact a diagnosis or a therapy decision.

Referring to FIG. 1, data at State 1 102 is acquired for a particular subject, such as, e.g., a patient. The patient data may include measurement data, medical image data, patient demographic information, or any other data of the patient. The patient data may be measured using a measurement device, computed by using a bio-physical computation, or a combination of both. Based on patient data 102, a quantity of interest (QoI) of the patient at State 1 104 is determined. In one embodiment, the QoI represents a medical characteristic of a patient. For example, a QoI of a patient may be the cardiac output of a patient's heart, the pressure drop in an artery of a patient, or any other medical characteristic of the patient. The QoI of the patient at State 1 104 is determined based on the QoI that is to be determined for the patient at State 2. A trained mapping function is applied to map the QoI of the patient at State 1 104 to the QoI of the patient at State 2 106 to determine the QoI of the patient at State 2 106. The trained mapping function extracts features from patient data at State 1 102 to map the QoI of the patient at State 1 104 to the QoI of the patient at State 2 106. The extracted features depend on the QoI that is to be determined for the patient at State 2. The particular features which are extracted may be learned by the trained mapping function in an offline training phase using training data. Advantageously, framework 100 may provide for a QoI of a patient at State 2 106 using data obtained for a patient at State 1 and does not rely on measurements or biophysical computations for the patient at State 2.

Figure 2:
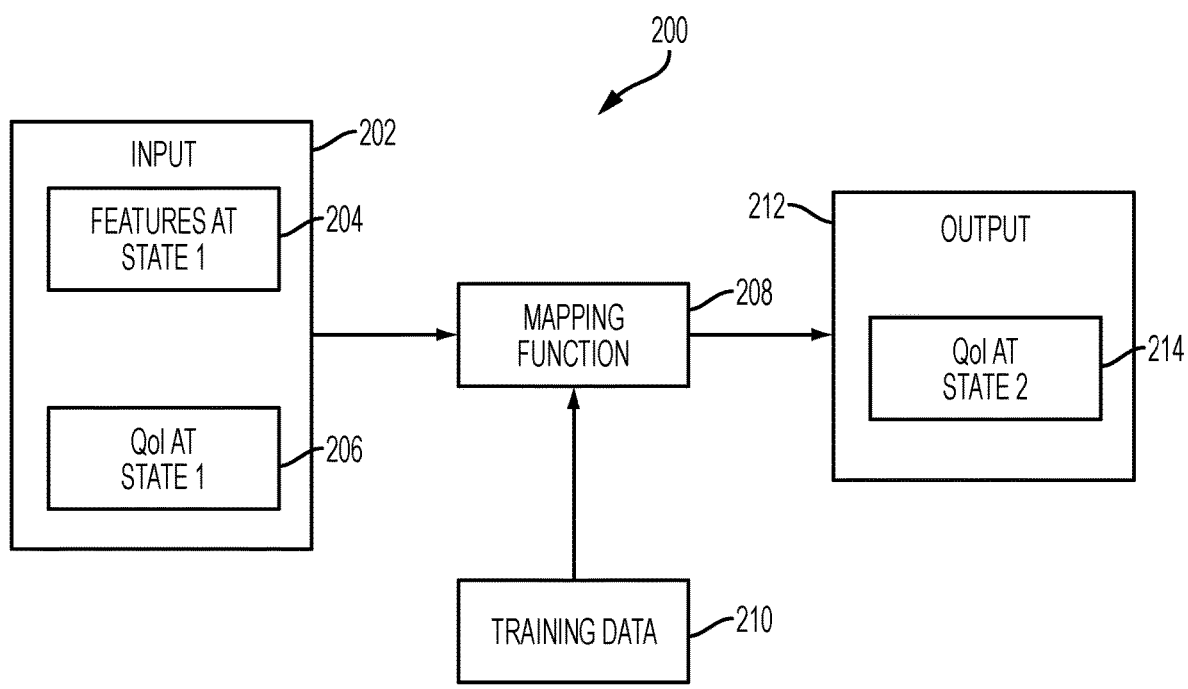
FIG. 2 shows a system for mapping patient data at one physiological state to another physiological state, in accordance with one embodiment.

FIG. 2 shows a system 200 for mapping patient data at one physiological state to another physiological state, in accordance with one or more embodiments. System 200 includes input 202 comprising features 204 extracted from patient data at State 1 and QoI of the patient at State 1 206. Features 204 and QoI at State 1 206 may be extracted from data of a patient at State 1. Patient data at State 1 may be acquired using one or more measurement devices, computed by simulation (e.g., performing a biophysical computation using a mathematical or physical model) based on medical image data of the patient, or a combination of both. The one or more measurement devices may include any device (e.g., invasive or non-invasive) capable of being used to provide measurement data of a subject, such as, e.g., an imaging device, a pressure wire, etc. The biophysical computation may include simulations, e.g., based on medical image data of the patient. For example, medical image data of the patient may be used to simulate, e.g., blood flow, pressure values, etc. The results of the simulations may be provided as the patient data.

Features 204 that are extracted from patient data at State 1 may depend on the QoI that is to be determined for the patient at State 2. Features 204 may include, e.g., anatomical features (e.g., geometry of a vessel), functional features (e.g., vital statistics, blood pressure, heart rate, oxygen saturation), or any other pertinent data. Anatomical features may be extracted from, e.g., medical image data of a patient at State 1, such as medical image data from magnetic resonance imaging (MRI), computed tomography (CT), X-ray angiography, ultrasound, or any other suitable imaging modality. For example, anatomical features such as a length of an anatomical structure may be determined by processing the medical image data to extract features 204. Functional features may be, e.g., measured invasively or non-invasively. Such measurements may be determined directly from the patient data to extract features 204. The particular features 204 that are extracted may be learned by mapping function 208 using training data 210.

For example, in the case of a cardiac disease patient, it is of interest to determine cardiac output as the QoI of a patient at State 2 (e.g., an exertion state). Cardiac output is the amount of blood that a patient's heart pumps out. Features 204 that are extracted from patient data at State 1 (e.g., a rest state) are based on the QoI of cardiac output to be determined for a patent at State 2. Features at State 1 204 for the QoI of cardiac output may include, e.g., the blood pressure at various chambers of the heart and the blood pressure in the aorta, which may be measured invasively or non-invasively as part of the patient data.

A value of QoI at State 1 206 may also be extracted from the patient data at State 1. The value of QoI at State 1 206 may be extracted from patient data at State 1 in a similar manner as features 204. For example, the patient data at State 1 may include medical image data, which may be processed to determine a value of the QoI of cardiac output of a patient at State 1. Cardiac output can be extracted from medical images by segmenting the heart chambers or by direct flow measurement using Doppler ultrasound, phase contrast MRI, or any other suitable technique. In another example, patient data at State 1 may include blood flow measurements (e.g., measured or simulated) to provide a value of the QoI of cardiac output of a patient at State 1.

In one embodiment, QoI at State 1 corresponds to a same quantity of interest desired at State 2. For instance, in the example of the cardiac disease patient above, where the quantity of interest at State 2 is the cardiac output at State 2, QoI at State 1 206 is the cardiac output at State 1. In other embodiments, QoI at State 1 206 may be used to determine a different QoI at State 2 214. QoI at State 1 206 may include a plurality of quantities of interest where there are multiple quantities of interest desired at State 2.

Mapping function 208 receives input 202 (comprising features at State 1 204 and QoI at State 1 206) to determine a value of QoI at State 2 214 as output 212. The goal of mapping function 208 is to compute a value of the QoI (e.g., the cardiac output) if the patient were at some other physiological state (i.e., State 2), which is distinct from the physiological state from which measurements/computations were performed (i.e., State 1). For example, mapping function 208 may be used to compute a value of the QoI of cardiac output during treadmill exercises based on measurements/computations of the patient at rest without subjecting the patient to the treadmill exercises, and thereby without making any new measurements. In another example, mapping function 208 may be used to compute the QoI of cardiac output when the patient is under a drug induced hyperemia condition without actually administering the drug to the patient.

Mapping function 208 may be a trained mathematical transformation that maps QoI at State 1 206 to QoI at State 2 214. It should be understood that the mapping relies on patient data from State 1, and not on any measurements/computations of the patient at State 2. However, in some embodiments, where patient data of the patient at Stage 2 is available, this patient data of the patient at Stage 2 may also be used by the trained mapping function 208 to determine QoI at State 2 214. Mapping function 208 may be represented as function $f$ in equation (1) below.

$$QoI(State2)=f(QoI(State1),Features(State1)) \qquad (1)$$

In equation (1), QoI(State 2) represents the quantity of interest at State 2 214, which is represented as a function of the quantity of interest at State 1 206 and features extracted from patient data at State 1 204. As can be seen from equation (1), QoI at State 2 214 depends only on measurements/computations from the patient at State 1.

The function $f$ in equation (1) may be any suitable function that can represent relationships between a QoI at State 1 and the QoI at State 2. For example, function $f$ may be determined using a machine learning based method, a parameter tuning approach, an optimization approach, a statistical approach, a data-driven approach, a control system based approach, etc.

In one embodiment, mapping function 208 is trained to learn relationships between the QoI at State 1 and the QoI at State 2 using training data 210 in an offline step, which may be performed at a previous point in time. Mapping function 208 learns which features from the patient data are relevant for mapping the QoI at State 1 and the QoI at State 2 from training data 210. The relationships learned between the QoI at State 1 and the QoI at State 2 may be for all patients, a particular subgroup of patients, or distinct for each individual (i.e., patient specific). Training data 210 may include, e.g., a patient database for which the QoI at State 1 and the corresponding QoI at State 2 are available. Training data 210 may include historical patient data (e.g., for all patients, a particular group of patients, a distinct patient), synthetic patient data (e.g., generated using simulations without any patient specific data), patient data obtained from bench-top experiments, etc.

For example, in one embodiment, mapping function 208 may employ a parameter estimation approach, which estimates parameters of the function $f$ (e.g., QoI at State 1 and features at Stage 1) for a QoI at State 2 using test data where corresponding QoI at State 2 is available.

In another example, mapping function 208 may include a machine learning based algorithm. Machine learning based algorithms include a training phase and a testing phase. The training phase represents the offline portion of the process, where function $f$ is determined by fitting input data (e.g., QoI at State 1 and patient data at State 1) to a ground truth (i.e., QoI at State 2) using training data. The training data includes the QoI at State 1 and a corresponding QoI at State 2 for a set of patients. Mapping function 208 may be determined using any machine learning based algorithm, such as, e.g., linear or non-linear regression, neural networks, support-vector machines, etc. The testing phase refers to the use of the trained machine learning based algorithm for an unseen case (i.e., a new case that was not used for training). In the testing phase, QoI at State 1 206 and features at State 1 204 are used by the trained machine learning based algorithm to compute QoI at State 2 214.

In an additional example, mapping function 208 may include a control systems based approach. In this approach, mapping function 208 is represented as a transfer function which maps QoI at State 1 206 (i.e., input) to the QoI at State 2 214 (i.e., output), using features of patient data at State 1 204 to model the system that is to be controlled. The function $f$ is obtained by designing a controller (using any control design algorithm) that maps the input to the output.

Mapping function 208 receives features of the patient at state 1 204 and QoI at State 1 206 as input 202 and provides QoI at State 2 214 as output 212. It should be understood that the embodiments described herein are not limited to State 1 and State 2, but may also be applied for more than two states by, e.g., concatenating the mathematical transformation in mapping function 208 or by performing the mapping function 208 in a repeated manner. Additionally, multiple QoI at State 1 may be available and may each be mapped by mapping function 208 to a same or different mapping to their respective QoI at Stage 2. Advantageously, system 200 determines a quantity of interest of a patient at State 2 based on data of the patient at State 1 and without relying on measurements or computations of the patient at State 2. System 200 thus provides a user with fast access to information that can impact a diagnosis or a therapy decision.

Figure 3:
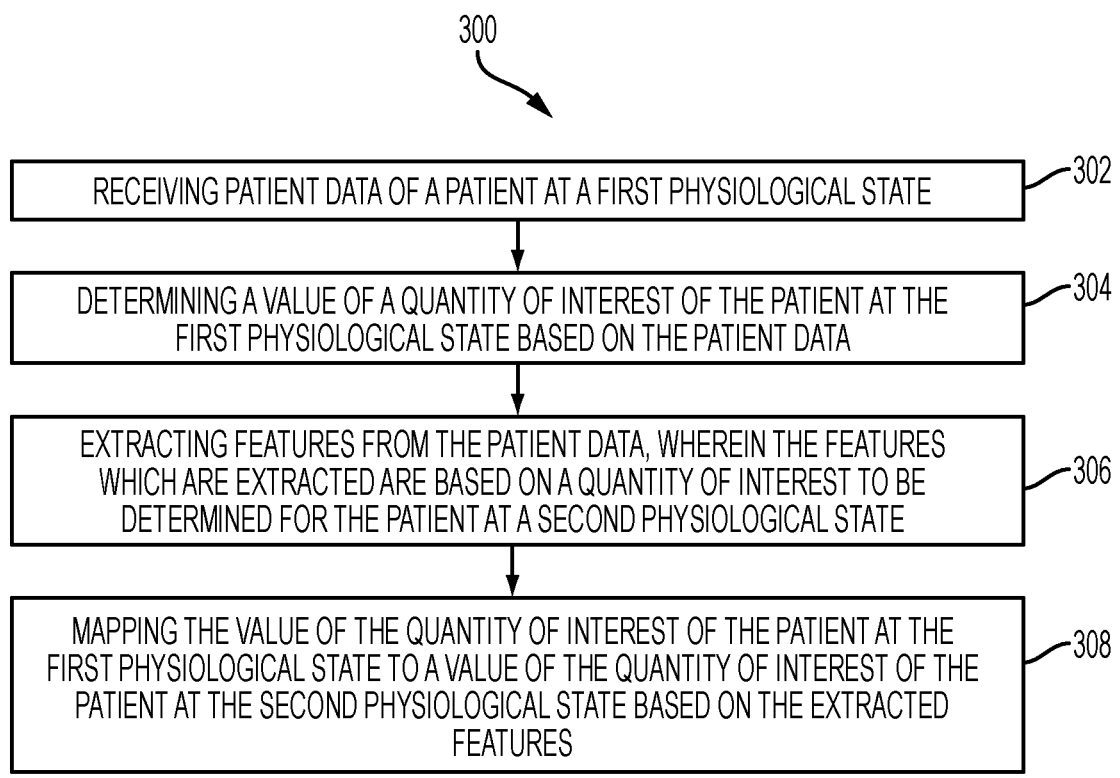
FIG. 3 shows a method for mapping patient data from one physiological state to another physiological state, in accordance with one embodiment.

FIG. 3 shows a method 300 for mapping patient data from a first physiological state (e.g., a rest state) to a second physiological state (e.g., an exertion state), in accordance with one or more embodiments. At step 302, patient data of a patient at a first state is received. The patient data may include any data of the patient, such as, e.g., anatomical data, functional data, etc., which may be acquired using one or more measurement devices, computed by simulation, or a combination of both. The one or more measurement devices may include, e.g., a medical device, a medical imaging device, etc. In one embodiment, the patient data may be received by receiving medical image data of a patient. The patient data may also be received as simulation results computed based on the medical image data. The medical image data may include imaging from, e.g., an MRI, CT, X-ray, ultrasound, or any other imaging modality. The medical image data may be received directly from the medical imaging device or may be received by loading a previously stored medical image of the patient.

At step 304, a value of a quantity of interest of the patient at the first physiological state is determined based on the patient data. In one embodiment, the quantity of interest represents a medical characteristic of the patient. The value of the quantity of interest of the patient at the first physiological state may be determined directly from the patient data or may be computed or calculated using the patient data. For example, the value of the quantity of interest of the patient at the first physiological state may include blood flow measurements that can be measured or simulated to provide the value of the quantity of interest of the patient at the first physiological state. In one embodiment, the quantity of interest of the patient at the first physiological state corresponds to a same quantity of interest to be determined for the patient at the second physiological state. In other embodiments, the quantity of interest of the patient at the first physiological state may be used to determine a different quantity of interest of the patient at the second physiological state.

At step 306, features are extracted from the patient data. The features which are extracted are based on the quantity of interest to be determined for the patent at the second physiological state. The features may include anatomical features and functional features. The anatomical features may be extracted from, e.g., medical image data of the patient. The functional features may be measured (e.g., invasively or non-invasively). For example, for a quantity of interest of cardiac output, the features extracted from the patient data may include the blood pressure at various chambers of the heart and the blood pressure of the aorta. The features in this example may be extracted by processing medical image data of the patient or determined directly from the patient data as measurements or simulation results. In another example, for a quantity of interest of pressure drop in an artery, the features extracted from the patient data may include the anatomical features such as the geometry of the vessel and functional features such as blood pressure, heart rate, oxygen saturation and other vital statistics of the patient. In a further example, for a quantity of interest of pressure drop before and after stenting, the features may include anatomical aspects of the vessel and properties of the stent (e.g., length, diameter).

At step 308, the quantity of interest of the patient at the first physiological state is mapped to the quantity of interest of the patient at the second physiological state based on the extracted features. The mapping may be performed by applying a trained mapping function on the extracted features of the patient at the first physiological state and the quantity of interest of the patient at the first physiological state to determine the quantity of interest of the patient at the second physiological state. The trained mapping function may be any function that can represent the relationships between the quantity of interest at the first state and the quantity of interest at the second state for a set of patients. For example, the trained mapping function may be trained using a machine learning based method, a parameter tuning approach, an optimization approach, a statistical approach, a data-driven approach, a control system based approach, etc. The trained mapping function may be trained in an offline step based on training data, such as, e.g., historical patient data, synthetic patient data, patient data obtained from bench-top experiments, etc.

In one embodiment, where there are multiple quantities of interest to be determined for a patient at the second state, steps 304 and 306 may be repeated for each quantity of interest.

Figure 4:
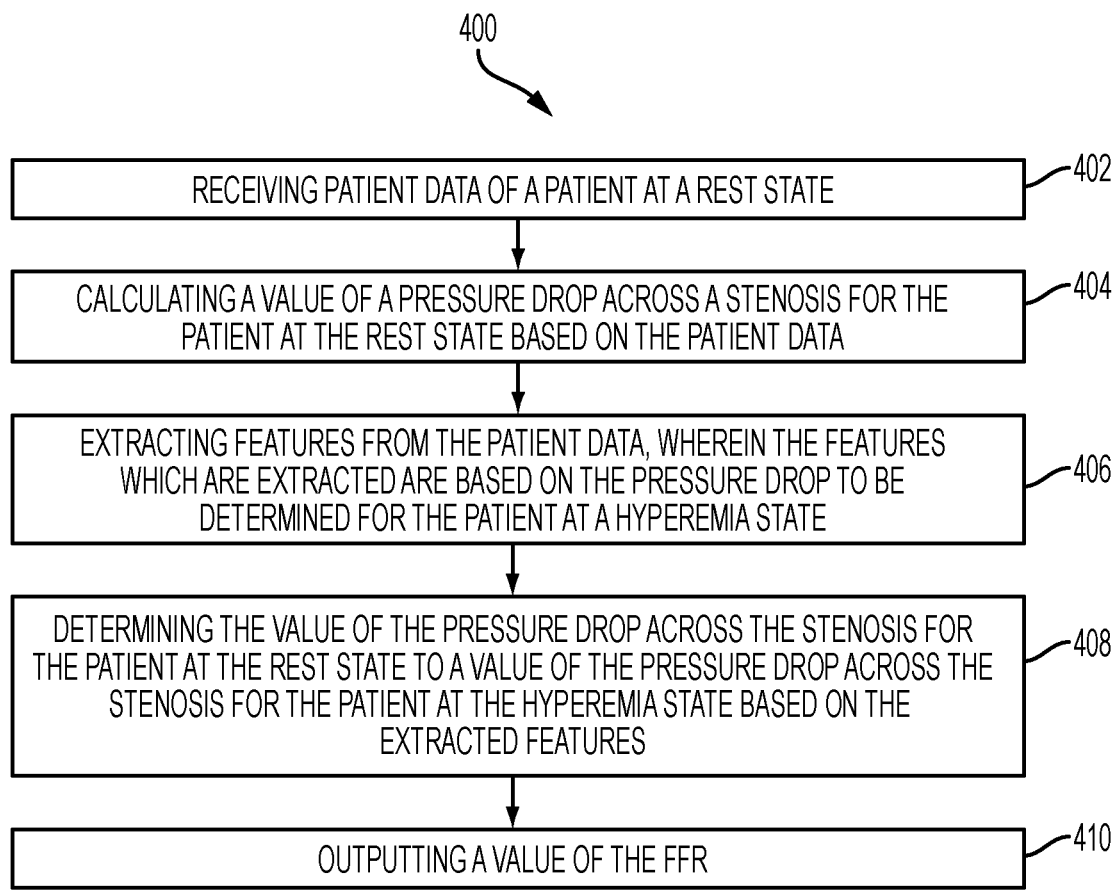
FIG. 4 shows an exemplary method for mapping a pressure drop of a patient at a hyperemia state from data of the patient at a rest state, in accordance with one embodiment.

FIG. 4 shows an exemplary method 400 for determining the Fractional Flow Reserve (FFR) for a stenosis of a patient, in accordance with one or more embodiments. FFR is a functional measure for quantifying the hemodynamic significance of a stenosis in an artery. FFR is typically determined based on the pressure drop over a coronary stenosis at hyperemia using invasive pressure wire based measurements. Hyperemia refers to a physiological state of the patient with more than normal blood flow. According to an embodiment of the present invention, FFR can instead be determined by mapping a pressure drop over an artery (e.g., coronary artery) of a patient at a rest state to a pressure drop at hyperemia. The pressure drop is an important physiological quantity that is of clinical interest, and is used to characterize the functional severity of a stenosis (narrowing of the vessel wall).

The conventional approach to determine the pressure drop during hyperemia would be to either directly measure the pressure drop during hyperemia or use a computational fluid dynamics (CFD) algorithm that simulates a hyperemia (by employing appropriate boundary conditions in the CFD algorithm and using the results of the CFD computation to determine the pressure drop at hyperemia). However, both of these conventional approaches have drawbacks. The measurement process is invasive, costly, and inherently risky for the patient since it is an additional clinical procedure. The CFD based computation is non-invasive, but may be time intensive and inaccurate due to the difficulty in obtaining the correct boundary conditions that represent the hyperemia state for a particular patient.

Referring to FIG. 4, at step 402, patient data is received for a patient at a rest state. The patient data may include, e.g., pressure measurements of a patient at rest (e.g., using a pressure wire). The patient data may also include, e.g., medical image data of the patient at rest, which may be used to perform a blood flow simulation over the, e.g., coronary artery stenosis using rest state boundary conditions (e.g., determined from medical image data and/or other non-invasive measurements). For example, such simulations may be performed using the method described in U.S. patent application Ser. No. 13/794,113, entitled "Method and System for Non-Invasive Functional Assessment of Coronary Artery Stenosis," and U.S. patent application Ser. No. 14/070,810, entitled "Method and System for Non-Invasive Functional Assessment of Coronary Artery Stenosis," which are incorporated herein by reference.

At step 404, a value of a pressure drop across a stenosis for the patient at the rest state is determined. The pressure drop may be any value indicating the drop in pressure across a, e.g., stenosis. For example, the pressure drop, $\Delta P$, may be represented as a difference between pressure distal to the stenosis, $Pd$, and pressure proximal to the stenosis, $Pa$, such that $\Delta P = Pd - Pa$. Pressure drop, $\Delta P$, may also be represented as a ratio between $Pd$ and $Pa$, such that $\Delta P = Pd/Pa$. Other representations are also contemplated. Distal and Proximal pressure may be extracted from medical image data or determined directly from patient data as measurements or simulation results. For example, the pressure may be measured invasively by, e.g., inserting a pressure wire into the artery. The pressure may also be measured by computing a CFD algorithm. Rest state measurements can be measured more easily, safely, cheaply, and quickly than hyperemic measurements since they do not require the patient to be in a hyperemic state.

At step 406, features are extracted from the patient data. The extracted features are based on the QoI (i.e., pressure drop across a stenosis) to be determined for the patient at the hyperemia state. In this example, the features may include anatomical features, such as features representing the geometry of the vessel, (e.g., length of the stenosis, radius of the vessel at/before/after the stenosis). The anatomical features may be extracted by processing medical image data to determine the geometry of the vessel. The features may also include function features such as vital statistics (e.g., blood pressure, heart rate, and oxygen saturation) of the patient at the rest state. The functional features may be determined as measurements or simulation results directly from the patient data.

At step 408, the pressure drop across the stenosis for the patient at the rest state is mapped to a pressure drop across the stenosis for the patient at the hyperemia state based on the features extracted at step 406. The mapping determines the pressure drop across the stenosis for the patient at the hyperemia state based on the pressure drop across the stenosis for the patient at the rest state, without subjecting the patient to hyperemia, or performing any measurements or biophysical computations at hyperemia.

The mapping may be generally represented as equation (2) to determine the change in pressure ΔP at hyperemia.

$$\Delta P(\text{hyperemia}) = f(\Delta P(\text{rest}), \text{Features}(\text{rest})) \quad (2)$$

The mapping function $f$ may be determined using, e.g., machine learning, an optimization approach, a statistical approach, a data-driven approach, a control system based approach, or any other suitable function that can represent relationships between the pressure drop across the stenosis for a patient at the rest state and the pressure drop across the stenosis for a patient at the hyperemia state. The mapping function $f$ may be trained in an offline step using training data. The training data may include pressure drops across a stenosis for a set of patients at a rest state and at a hyperemia state. The pressure drops across a stenosis may be computed based on, e.g., actual blood flow measurements for the set of patients at a rest state and at a hyperemia state, simulated blood flow measurements for the set of patients at a rest state and at a hyperemia state, or a combination of both. The set of patients used in the training may be all patients having pressure drop data available at a rest state and at a hyperemia state, a particular subclass of patients (e.g., based on demographics, medical history, family history, etc.), or may be patient specific (e.g., using data from that specific patient).

In one embodiment, the pressure drop across the stenosis for the patient at the hyperemia state may be determined by first determining, at the rest state, a pressure distal to the stenosis, Pd(rest), and a pressure proximate to the stenosis, Pa(rest), and then mapping Pd(rest) and Pa(rest) individually to the hyperemia state values, Pd(hyperemia) and Pa(hyperemia), respectively. The pressure drop across the stenosis can then be calculated for a patient at the hyperemia state based on Pd(hyperemia) and Pa(hyperemia). In another embodiment, the pressure drop across the stenosis for the patient at the hyperemia state may be determined by first determining a pressure drop across the stenosis for the patient at the rest state (e.g., ΔP=Pd/Pa), and then mapping the pressure drop across the stenosis for the patient at the rest state ΔP(rest) to the pressure drop across the stenosis for the patient at the hyperemia state ΔP(hyperemia), as shown in equation (3).

$$P_d/P_a(\text{hyperemia}) = f(P_d/P_a(\text{rest}), \text{Features}(\text{rest})) \quad (3)$$

At step 410, the FFR of the stenosis for the patient at the hyperemia state is outputted. The FFR of a stenosis is a representation of the pressure drop across the stenosis for a patient at hyperemia. The FFR for a stenosis may be represented as in equation (4).

$$\text{FFR} = P_d/P_a(\text{hyperemia}) \quad (4)$$

In some embodiments, the FFR of a stenosis for a patient at a hyperemia state may be determined using a different rest state metric. For example, the instantaneous wave-free ratio (iFR) of a patient at a rest state may be mapped to the FFR of the stenosis for the patient at a hyperemia state based on features extracted from patient data of a patient at the rest state. The mapping may be represented as equation (5).

$$\text{FFR}(\text{hyperemia}) = f(i\text{FR}(\text{rest}), \text{Features}(\text{rest})) \quad (5)$$

In another example, a quantity of interest of a patient in a post-intervention state may be determined without actually performing the intervention or explicitly measuring/computing the QoI in the post-intervention state. Conventional techniques for predicting the effect of an intervention on a quantity of interest rely on first performing a virtual intervention (e.g., modifying an anatomical model of an organ to simulate the effect of the intervention on the anatomy) and then computing the physiological metrics in the post-intervention state by performing biophysical computations.

In accordance with one embodiment, a QoI of a patient in the post-intervention state may be determined based on the QoI of the patient in the pre-intervention state and features of the patient in the pre-intervention state. The intervention may be, e.g., a stenting procedure whereby the stenosis in a blood vessel is treated by inserting a stent and dilating it in order to ease constriction. This allows for blood to flow more easily, thereby alleviating the pressure drop. In order to ascertain whether the stenting procedure was successful and to plan in case of multiple stenosises, one would benefit from the knowledge of the potential post-intervention pressure drop even before performing the intervention. The mapping of the pressure drop of a patient in a pre-stenting state can be mapped to determine the pressure drop of a patient in a post-stenting state based on features of the patient data in the pre-stenting state. The features of the patient data in the pre-stenting state may include anatomical aspects of the vessel, properties of the stent (e.g., length of the stent, diameter of the stent), etc. The mapping may be represented in equation (6).

$$\Delta P(\text{post-stent}) = f(\Delta P(\text{pre-stent}), \text{Features}(\text{pre-stent})) \quad (6)$$

Other examples of interventions may include invasive, minimally invasive, or non-invasive interventions that may utilize a medical device (e.g., implanted or used to perform the intervention). For example, the intervention may include a stent therapy, a flow diverter therapy, an ablation therapy, an electrical simulation therapy, a vascular surgery, etc. The interventions may also include pharmaceutical interventions. Examples of pharmaceutical interventions include blood pressure lowering drugs, a vasodilator or vasoconstriction drug, etc.

It should be understood that the embodiments discussed herein may be applied to determine any quantity of interest at any state. For example, for cardiac resynchronization therapy (CRT), quantities of interest may include, e.g., electrocardiography (ECG) (e.g., QT wave duration) and activation time, which may be determined for a post-implant stage (i.e., after the CRT device is implanted in the heart) based on quantities of interest at a pre-implant stage and features extracted from patient data acquired at the pre-implant stage, where the features may include features based on cardiac anatomy, flow, mechanics and electrophysiology, CRT device parameters, etc. In another example, for aortic valve stenting, quantities of interest may include, e.g., trans-stenotic pressure drop, para-valvular leakage, and peak velocity, which may be determined for a post-implant stage (i.e., after the stent is implanted in the aortic valve) based on quantities of interest at a pre-implant stage and features extracted from patient data acquired at the pre-implant stage, where the features may include, e.g., valve, aorta, and outflow tract anatomy, blood pressure, and stent size.

It should further be understood that the embodiments discussed herein are not limited to the medical field, but may be employed to determine any quantity of interest for any subject at a second state based on data of the subject at a first state.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the method steps described herein, including one or more of the steps of FIGS. 3 and 4. Certain steps of the methods described herein, including one or more of the steps of FIGS. 3 and 4, may be performed by a server or by another processor in a network-based cloud-computing system. Certain steps of the methods described herein, including one or more of the steps of FIGS. 3 and 4, may be performed by a client computer in a network-based cloud computing system. The steps of the methods described herein, including one or more of the steps of FIGS. 3 and 4, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIGS. 3 and 4, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 5:
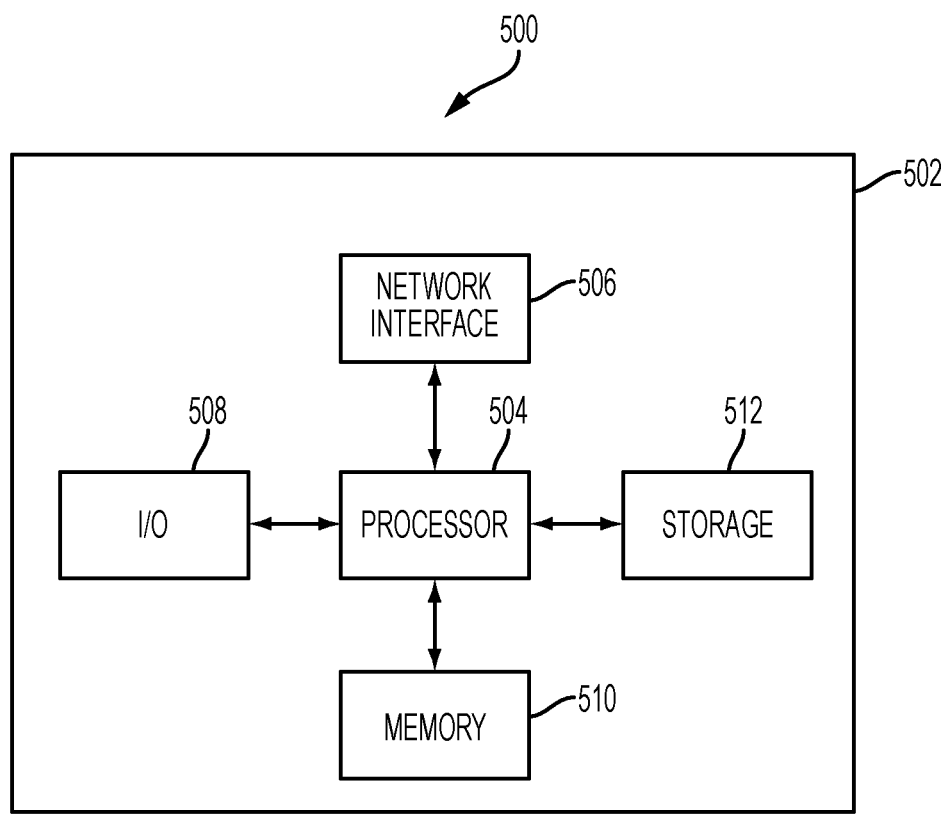
FIG. 5 shows a high-level block diagram of a computer for mapping patient data at one physiological state to another physiological state, in accordance with one embodiment.

A high-level block diagram 500 of an example computer that may be used to implement systems, apparatus, and methods described herein is depicted in FIG. 5. Computer 502 includes a processor 504 operatively coupled to a data storage device 512 and a memory 510. Processor 504 controls the overall operation of computer 502 by executing computer program instructions that define such operations. The computer program instructions may be stored in data storage device 512, or other computer readable medium, and loaded into memory 510 when execution of the computer program instructions is desired. Thus, the method steps of FIGS. 3 and 4 can be defined by the computer program instructions stored in memory 510 and/or data storage device 512 and controlled by processor 504 executing the computer program instructions. For example, the computer program instructions can be implemented as computer executable code programmed by one skilled in the art to perform the method steps of FIGS. 3 and 4. Accordingly, by executing the computer program instructions, the processor 504 executes the method steps of FIGS. 3 and 4. Computer 502 may also include one or more network interfaces 506 for communicating with other devices via a network. Computer 502 may also include one or more input/output devices 508 that enable user interaction with computer 502 (e.g., display, keyboard, mouse, speakers, buttons, etc.).

Processor 504 may include both general and special purpose microprocessors, and may be the sole processor or one of multiple processors of computer 502. Processor 504 may include one or more central processing units (CPUs), for example. Processor 504, data storage device 512, and/or memory 510 may include, be supplemented by, or incorporated in, one or more application-specific integrated circuits (ASICs) and/or one or more field programmable gate arrays (FPGAs).

Data storage device 512 and memory 510 each include a tangible non-transitory computer readable storage medium. Data storage device 512, and memory 510, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 508 may include peripherals, such as a printer, scanner, display screen, etc. For example, input/output devices 508 may include a display device such as a cathode ray tube (CRT) or liquid crystal display (LCD) monitor for displaying information to the user, a keyboard, and a pointing device such as a mouse or a trackball by which the user can provide input to computer 502.

Any or all of the systems and apparatus discussed herein, including elements of system 200 of FIG. 2, may be implemented using one or more computers such as computer 502.

One skilled in the art will recognize that an implementation of an actual computer or computer system may have other structures and may contain other components as well, and that FIG. 5 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for determining a quantity of interest of a patient, comprising:
  receiving, using a processor, patient data of the patient at a first physiological state, wherein the patient data comprises medical image data of the patient;
  determining, using the processor, a value of a quantity of interest of the patient at the first physiological state based on a patient-specific computational fluid dynamics simulation of blood flow, the patient-specific computational fluid dynamics simulation performed using boundary conditions corresponding to the first physiological state determined based on the medical image data of the patient, the quantity of interest representing a medical characteristic of the patient;
  extracting, using the processor, features from the patient data, wherein the features which are extracted are based on the quantity of interest to be determined for the patient at a second physiological state; and
  mapping, using the processor, the value of the quantity of interest of the patient at the first physiological state to a value of the same quantity of interest of the patient at the second physiological state using a machine learning based mapping function based on the extracted features, the machine learning based mapping function receiving as input 1) the value of the quantity of interest of the patient at the first physiological state and 2) the extracted features and outputting the value of the same quantity of interest of the patient at the second physiological state,
  wherein the machine learning based mapping function is trained during an offline step using training data comprising values of the quantity of interest for a set of patients at the first physiological state and ground truth values of the same quantity of interest for the set of patients at the second physiological state.

2. The method as recited in claim 1, wherein mapping the value of the quantity of interest of the patient at the first physiological state to the value of the same quantity of interest of the patient at the second physiological state further comprises:
  mapping the value of the quantity of interest of the patient at the first physiological state to the value of the same quantity of interest of the patient at the second physiological state without using data of the patient at the second physiological state.

3. The method as recited in claim 1, wherein the machine learning based mapping function is trained to learn a relationship between the quantity of interest of a set of patients at the first physiological state and the same quantity of interest of the set of patients at the second physiological state.

4. The method as recited in claim 1, wherein the training data further comprises the quantities of interest of the set of patients simulated at the first physiological state and the same quantities of interest simulated at the second physiological state.

5. The method as recited in claim 1, the patient data comprises medical image data of the patient, and extracting features from the patient data comprises:
  processing the medical image data of the patient to determine measurements of the patient.

6. An apparatus for determining a quantity of interest of a patient, comprising:
  a memory storing computer program instructions; and
  at least one processor configured to execute the computer program instructions, the computer program instructions configured to cause the at least one processor to perform operations of:
  receiving patient data of the patient at a first physiological state;
  determining a value of a quantity of interest of the patient at the first physiological state based on a patient-specific computational fluid dynamics simulation of blood flow, the patient-specific computational fluid dynamics simulation performed using boundary conditions corresponding to the first physiological state determined based on the medical image data of the patient, the quantity of interest representing a medical characteristic of the patient;
  extracting features from the patient data, wherein the features which are extracted are based on the quantity of interest to be determined for the patient at a second physiological state; and
  mapping the value of the quantity of interest of the patient at the first physiological state to a value of the same quantity of interest of the patient at the second physiological state using a machine learning based mapping function based on the extracted features, the machine learning based mapping function receiving as input 1) the value of the quantity of interest of the patient at the first physiological state and 2) the extracted features and outputting the value of the same quantity of interest of the patient at the second physiological state,
  wherein the machine learning based mapping function is trained during an offline step using training data comprising values of the quantity of interest for a set of patients at the first physiological state and ground truth values of the same quantity of interest for the set of patients at the second physiological state.

7. The apparatus as recited in claim 6, wherein mapping the value of the quantity of interest of the patient at the first physiological state to the value of the same quantity of interest of the patient at the second physiological state further comprises:
  mapping the value of the quantity of interest of the patient at the first physiological state to the value of the same quantity of interest of the patient at the second physiological state without using data of the patient at the second physiological state.

8. The apparatus as recited in claim 6, wherein the machine learning based mapping function is trained to learn a relationship between the quantity of interest of a set of patients at the first physiological state and the same quantity of interest of the set of patients at the second physiological state.

9. The apparatus as recited in claim 6, wherein the training data further comprises the quantities of interest of the set of patients simulated at the first physiological state and the same quantities of interest simulated at the second physiological state.

10. A non-transitory computer readable medium storing computer program instructions for determining a quantity of interest of a patient, the computer program instructions when executed by a processor cause the processor to perform operations comprising:
  receiving patient data of the patient at a first physiological state;
  determining a value of a quantity of interest of the patient at the first physiological state based on a patient-specific computational fluid dynamics simulation of blood flow the patient-specific computational fluid dynamics simulation performed using boundary conditions corresponding to the first physiological state determined based on the medical image data of the patient, the quantity of interest representing a medical characteristic of the patient;

extracting features from the patient data, wherein the features which are extracted are based on the quantity of interest to be determined for the patient at a second physiological state; and mapping the value of the quantity of interest of the patient at the first physiological state to a value of the same quantity of interest of the patient at the second physiological state using a machine learning based mapping function based on the extracted features, the machine learning based mapping function receiving as input 1) the value of the quantity of interest of the patient at the first physiological state and 2) the extracted features and outputting the value of the same quantity of interest of the patient at the second physiological state, wherein the machine learning based mapping function is trained during an offline step using training data comprising values of the quantity of interest for a set of patients at the first physiological state and ground truth values of the same quantity of interest for the set of patients at the second physiological state.

11. The non-transitory computer readable medium as recited in claim 10, wherein mapping the value of the quantity of interest of the patient at the first physiological state to the value of the same quantity of interest of the patient at the second physiological state further comprises:

mapping the value of the quantity of interest of the patient at the first physiological state to the value of the same quantity of interest of the patient at the second physiological state without using data of the patient at the second physiological state.

12. The non-transitory computer readable medium as recited in claim 10, the patient data comprises medical image data of the patient, and extracting features from the patient data comprises:

processing the medical image data of the patient to determine measurements of the patient.

\* \* \* \* \*